(12) United States Patent
Doll et al.

(10) Patent No.: US 9,850,222 B2
(45) Date of Patent: Dec. 26, 2017

(54) CARBONATED ESTOLIDES AND METHODS OF MAKING AND USING THE SAME

(71) Applicant: The United States of America, as represented by the Secretary of Agriculture, Washington, DC (US)

(72) Inventors: Kenneth M. Doll, Peoria, IL (US); Terry Isbell, Elmwood, IL (US); Steven C. Cermak, Galesburg, IL (US); James A. Kenar, East Peoria, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/224,934

(22) Filed: Aug. 1, 2016

(65) Prior Publication Data

US 2017/0044128 A1 Feb. 16, 2017

Related U.S. Application Data

(60) Provisional application No. 62/204,628, filed on Aug. 13, 2015.

(51) Int. Cl.
*C07D 317/36* (2006.01)
*C07C 269/04* (2006.01)
*C07C 271/20* (2006.01)

(52) U.S. Cl.
CPC .......... *C07D 317/36* (2013.01); *C07C 269/04* (2013.01); *C07C 271/20* (2013.01)

(58) Field of Classification Search
CPC .... C07D 317/36; C07C 269/04; C07C 271/20
See application file for complete search history.

(56) References Cited

U.S. PATENT DOCUMENTS

| 7,045,577 B2 | 5/2006 | Wilkes et al. |
| 8,258,326 B1 | 9/2012 | Forest et al. |

OTHER PUBLICATIONS

Doll, Kenneth et al., Synthesis of Carbonated Fatty Methyl Esters Using Supercritical Carbon Dioxide, Journal Agriculture and Food Chemistry, (2005), 53:9608-9614.
Kenar, James, Functionalization of Oleyl Carbonate by Epoxidation, J. Amer Oil chem Sock, (2007), 84:457-461.
Doll, Kenneth et al. The improved synthesis of carbonated soybean oil using supercritical carbon dioxide at a reduced reaction time, Green Chemistry, (2005), 7(12):849-854.
Doll, Kenneth et al., Carbonates from oleochemicals Biobased materials to value added green chemicals, Chemistry Today, 25(6):7-10.
098754321'Mann, Noel et al., Synthesis of Carbonated Vernonia Oil, J. Am Oil Chem Soc, (2008), 85:791-796.
Kenar, James A. et al. Convenient preparation of fatty ester cyclic carbonates*, Eur. J. Lipid Sci. Technol., (2005), 107:135-137.

*Primary Examiner* — Timothy R Rozof
(74) *Attorney, Agent, or Firm* — G. Byron Stover; John D. Fado

(57) ABSTRACT

Disclosed herein are the conversion of estolide compounds having unsaturated fatty acid groups into estolides containing cyclic carbonate moieties and methods of making and using the same. The estolides containing a cyclic carbonate may be used to produce urethane containing estolides.

7 Claims, 9 Drawing Sheets

CARBONATED ESTOLIDES AND METHODS OF MAKING AND USING THE SAME

REFERENCE TO RELATED APPLICATION

This application claims the benefit of U.S. Provisional Application No. 62/204,628, filed 13 Aug. 2015, which is incorporated herein by reference in its entirety.

BACKGROUND OF THE INVENTION

Disclosed herein are the conversion of estolide compounds having unsaturated fatty acid groups into estolides containing carbonate moieties and methods of making and using the same.

The production of lubricating oils from natural products has been an area of significant study over the past couple of decades and steady incorporation of those products into the lubricant market has been made due to their good lubricity and biodegradability (Biermann, U., Angew. Chem. Int. Ed. Engl., 50: 3854-3871 (2011); Biresaw, G., et al., J. Am. Oil Chem. Soc., 80: 697-704 (2003); Wagner, H., et al., Appl. Catal., A, 221: 429-442 (2001)). Although biobased lubricants are an attractive replacement to petroleum lubricants, these natural materials suffer from performance issues due to poor cold temperature attributes, and poor oxidative and hydrolytic stabilities. To overcome these issues, vegetable oils can be chemically modified by introducing branching or reducing unsaturation in the molecule. An especially effective approach has been the development of a class of compounds known as estolides (Cermak, S., and T. Isbell, T., J. Am. Oil Chem. Soc., 78: 557-565 (2001a)). Estolides are biobased oligomeric esters obtained by the addition of a fatty acid to a hydroxyl containing vegetable oil or fat or by the condensation of a fatty acid across the olefin functionality of a vegetable oil or fat. The newly formed secondary ester groups not only makes the molecule more resistant to water hydrolysis as compared to underivatized triglycerides but also increases the branching within the molecule and dramatically improves the overall physical properties in certain applications compared to unmodified vegetable and mineral oils. In conjunction with these chemical attributes they exhibit excellent lubrication and viscosity characteristics (Cermak, S. C., et al., Ind. Crops Prod., 23: 54-64 (2006); Isbell, T. A., et al., Ind. Crops Prod., 23: 256-263 (2006)), and much improved stability toward oxidation (Cermak, S. C., and T. A. Isbell, U.S. Pat. No. 6,316,649 (2001b); Isbell, T. A., et al., U.S. Pat. No. 6,018,063 (2000)) making them useful as a basestock for functional fluid applications.

Fatty acid-based organic carbonates (aliphatic and cyclic) are an important class of compounds and exhibit interesting chemistry (Parrish, J. P., et al., Tetrahedron, 56: 8207-8237 (2000); Shaikh, A.-A. G., and S. Sivaram, Chem. Rev., 96: 951-976 (1996)) and applications including industrial fluids (Gryglewicz, S., et al., Ind. Eng. Chem. Res., 42: 5007-5010 (2003); Kenar, J. A., and I. D. Tevis, Eur. J. Lipid Sci. Technol., 107: 135-137 (2005); Kenar, J. A., et al., Journal of the American Oil Chemists' Society, 81(3): 285-291 (2004)). With regards to biobased cyclic carbonates, the 5-membered cyclic carbonate ring can be prepared from fatty ester chlorohydrins (Kenar, J. A., and I. D. Tevis, 2005) or from an epoxidized oil and carbon dioxide (Holser, R. A., Journal of Oleo Science, 56: 629-632 (2007)). In the later method, it was demonstrated that supercritical carbon dioxide was more effective than subcritical carbon dioxide to introduce the cyclic carbonate moiety onto the vegetable oils alkyl chain (Doll, K. M., and S. Z. Erhan, J. Agric. Food Chem., 53: 9608-9614 (2005b)). Although carbonated soybean oil is probably the most studied (Doll, K. M., and S. Z. Erhan, Green Chem., 7: 849-854 (2005a); Li, Z., et al., Catal Lett, 123: 246-251 (2008); Mazo, P., and L. Rios, J. Am. Oil Chem. Soc., 90: 725-730 (2013); Tamami, B., et al., J. Appl. Polym. Sci., 92: 883-891 (2004); Wilkes, G. L., et al., U.S. Pat. No. 7,045,577 (2006)), vernonia oil (Mann, N., et al., J. Am. Oil Chem. Soc., 85: 791-796 (2008)) and cottonseed oil (Zhang, L., et al., J. Am. Oil Chem. Soc., 91: 143-150 (2014)) have also been carbonated using carbon dioxide methodologies.

The ability to introduce the cyclic carbonate moiety onto other more complex biobased materials possessing unsaturation such as an estolide has not been investigated and would represent an interesting extension for this unique class of compounds. The carbonated estolides may have the advantages of the estolide structure as well as the potential chemical functionality exhibited by the cyclic carbonate group. Herein, we disclose estolide compounds containing carbonate moieties and methods of making and using the same. One example of the process is the conversion of unsaturated 2-ethylhexyl estolides into 5-membered cyclic carbonate groups through a two-step process utilizing an epoxidized estolide intermediate. The synthesis and characterization of these materials are described below.

SUMMARY OF THE INVENTION

Disclosed herein are the conversion of estolide compounds having unsaturated fatty acid groups into estolides containing carbonate moieties and methods of making and using the same.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

DETAILED DESCRIPTION OF THE INVENTION

Figure 1:
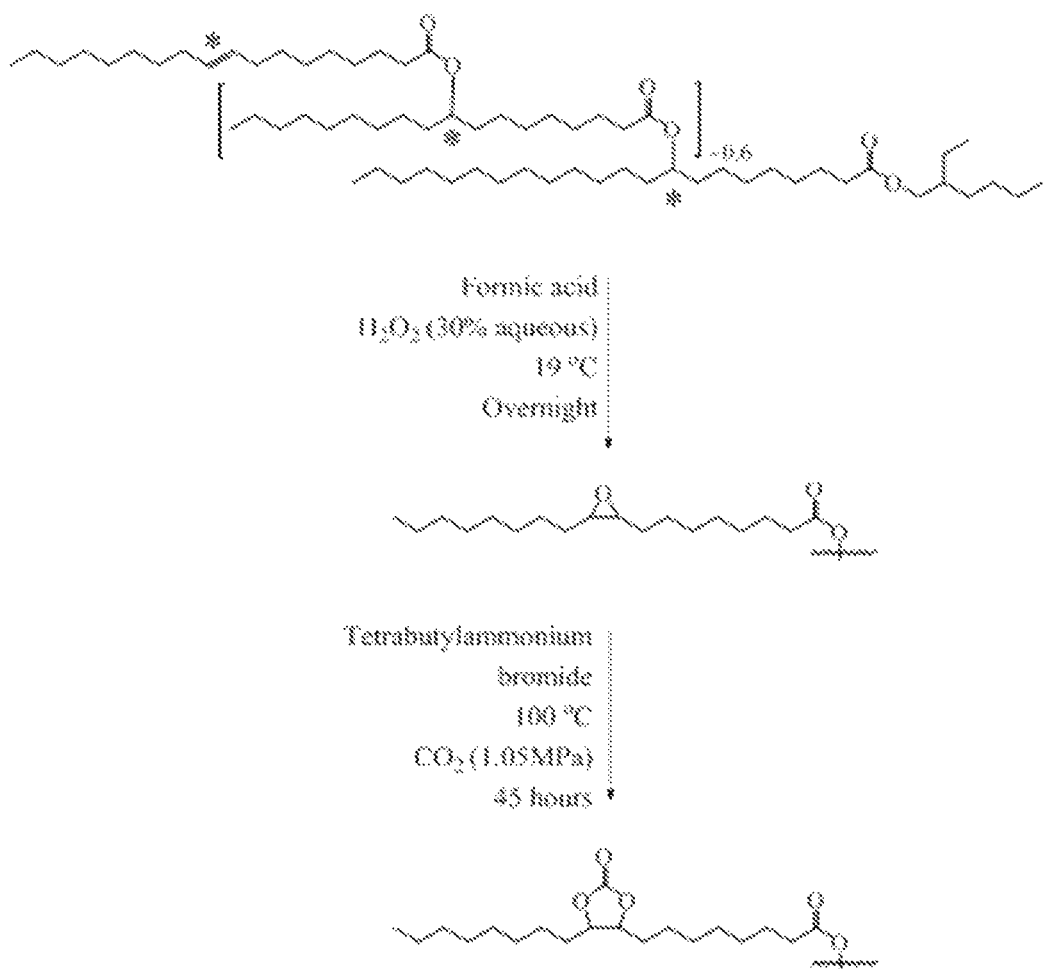
FIG. 1 shows the synthesis of a carbonated estolide using an epoxide route as described below. Although the original positions of unsaturation, 9 (or 9') and 10 (or 10'), have the greatest abundances, estolide positions have been observed distributed from positions 5-13 (or 5'-13') of the chain. Isomerization of the alkene to the expected cis and trans ratio was also evident.

We have now produced a family of novel estolide compounds derived from estolides having unsaturated fatty acid chains in their structure and which have unexpectedly high viscosities.

We have produced estolides containing a cyclic carbonate having the Formula

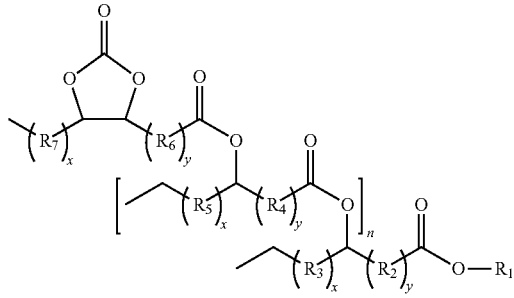

wherein x and y are each equal to 1 or greater than 1 (with an upper limit of 17) and x is independent from each occurrence (e.g., x could be 3 in one chain, but 4 or 5 in another chain; or x could be 1 in one chain, but 9 in another chain and 10 in yet another chain) and y is independent from each occurrence (e.g., y could be 3 in one chain, but 4 or 5 in another chain; or y could be 9 in one chain, and 1 in another chain and 3 in yet another chain) (preferred wherein x+y=14),
wherein n is 0-9 (n is preferably 1),
$R_1$ is H or an linear alkyl chain (e.g., C1-C14; for example, methyl, ethyl, propyl, octyl; preferably methyl) or a branched alkyl chain (e.g., C1-C14; for example, 2-ethylhexyl, 1-methylpentyl, isopropyl; preferably 2-ethylhexyl) or

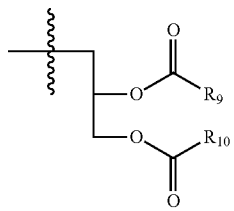

wherein $R_9$ and $R_{10}$ are independently selected from hydrogen and C1 to C36 hydrocarbon (preferably C12 to C22) which may be saturated or unsaturated, branched or straight chain, or substituted or unsubstituted (examples of ROO— include oleic, steric, butyric, lauric, myristic, palmitic, stearic, arachidic, behenic, lignoceric, oleic, linoleic, linolenic, petroselinic, ricinoliec, decanoic, octanoic, caproic acids; C1 to C36 hydrocarbon includes other fatty acid chain, or epoxidized fatty chain, or hydroxyl containing fatty chain, or carbonated fatty chain; carbonated fatty chain is defined as a hydrocarbon chain that contain a structure where two adjacent carbon atoms are bound to oxygen atoms that are bound to another carbon atom that is doubly bonded to an oxygen atoms; preferably $R_9$ and $R_{10}$ are substituted C18 hydrocarbon chains)
and $R_2$-$R_7$ are independently selected from —$CH_2$—, —C=C—, or

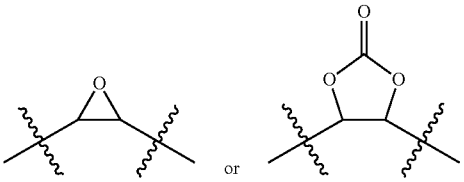 [SMILES: *C1OC1* ; *C1OC(=O)OC1*]

(curvy line indicate that these can be bonded anywhere in the chain).

The estolides containing a cyclic carbonate may be made by a method involving (a) reacting formic acid (e.g., about 0.1 to about 10000 g (e.g., 0.1-10000 g), preferably about 1 to about 1000 g (e.g., 1-1000 g), more preferably about 1 to about 100 g (e.g., 1-100 g), more preferably about 1 to about 20 g (e.g., 1-20 g), and most preferably about 11 g (e.g., 11 g)) and $H_2O_2$ (e.g., about 0.1 to about 10000 g (e.g., 0.1-10000 g), preferably about 1 to about 1000 g (e.g., 1-1000 g), more preferably about 1 to about 100 g (e.g., 1-100 g), more preferably about 1 to about 20 g (e.g., 1-20 g), and most preferably about 16 g (e.g., 16 g)), and at least one estolide compound (e.g., about 0.1 to about 10000 g (e.g., 0.1-10000 g), preferably about 1 to about 1000 g (e.g., 1-1000 g), more preferably about 1 to about 100 g (e.g., 1-100 g), more preferably about 1 to about 30 g (e.g., 1-30 g), and most preferably about 20 g (e.g., 20 g)) of the Formula

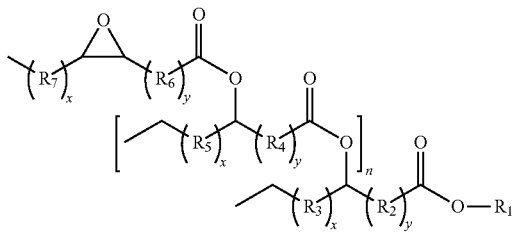

wherein x and y are each equal to 1 or greater than 1 (with an upper limit of 22) and x is independent from each occurrence (e.g., x could be 3 in one chain, but 4 or 5 in another chain; or x could be 1 in one chain, but 9 in another chain and 10 in yet another chain) and y is independent from each occurrence (e.g., y could be 3 in one chain, but 4 or 5 in another chain; or y could be 9 in one chain, and 1 in another chain and 3 in yet another), wherein n is 0-9, $R_1$ is H, or an linear alkyl chain (e.g., C1-C14; for example, methyl, ethyl, propyl, octyl; preferably C12 to C22) or a branched alkyl chain (e.g., C1-C14; for example, 2-ethylhexyl, 1-methylpentyl, isopropyl; preferably are substituted C18 hydrocarbon chains)) or

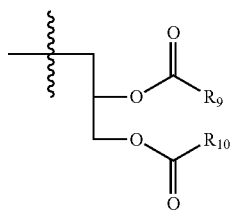

wherein $R_9$ and $R_{10}$ are independently selected from hydrogen and C-1 to C-36 hydrocarbon (preferably C12 to C22) which may be saturated or unsaturated, branched or straight chain, or substituted or unsubstituted (examples of ROO— include oleic, steric, butyric, lauric, myristic, palmitic, stearic, arachidic, behenic, lignoceric, oleic, linoleic, linolenic, petroselinic, ricinoliec, decanoic, octanoic, caproic acids; C-1 to C-36 hydrocarbon includes other fatty acid chain, or epoxidized fatty chain, or hydroxyl containing fatty chain, or carbonated fatty chain; carbonated fatty chain is defined as a hydrocarbon chain that contain a structure where two adjacent carbon atoms are bound to oxygen atoms that are bound to another carbon atom that is doubly bonded to an oxygen atoms; preferably $R_9$ and $R_{10}$ are substituted C18 hydrocarbon chains)), and $R_2$-$R_7$ are independently selected from —$CH_2$—, —C=C—, or

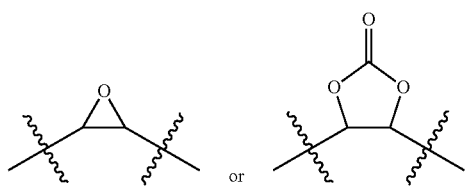 [SMILES: *C1OC1* ; *C1OC(=O)OC1*]

for about 1 to about 40 hours (e.g., 1-40 hours; preferably about 4 to about 24 hours (e.g., 4-24 hours), more preferably about 6 to about 10 hours (e.g., 6-10 hours), most preferably about 8 hours (e.g., 8 hours)) at temperatures of about 0° to about 99° C. (e.g., 0° to 99° C.; preferably about 0° to about 30° C. (e.g., 0° to 30° C.), more preferably about 0° to about 19° C. (e.g., 0° to 19° C.)) with rapid stirring to form epoxidized estolide, and (b) reacting the epoxidized estolide with an alkylammonium salt (e.g., tetrabutylammonium bromide; about 1 to about 25 wt % (e.g., 1 to 25 wt %; preferably about 2 to about 10 wt % (e.g., 2 to 10 wt %), more preferably about 5 wt % (e.g., 5 wt %)) compared to epoxidized estolide and pressurized $CO_2$ under supercritical conditions (e.g., about 1 to about 10000 psi (e.g., 1 to 10000 psi), preferably about 14 to about 3000 psi (e.g., 14 to 3000 psi), more preferably about 500 to about 2000 psi (e.g., 500 to 2000 psi), more preferably about 1300 to about 1700 psi (e.g., 1300 to 1700 psi), most preferably about 1500 psi (e.g., 1500 psi)) at temperatures of about 50° to about 200° C. (e.g., 50° to 200° C.; preferably about 70° to about 150° C. (70° to about 150° C.), more preferably about 90° to about 110° C. (90° to about 110° C.), most preferably about 100° C. (e.g., 100° C.)) for about 1 to about 168 hours (e.g., 1 to 168 hours; preferably about 12 to about 72 hours (e.g. 12 to 72 hours), more preferably about 25 to about 60 hours (e.g., 25 to 60 hours), more preferably about 40 to about 50 hours (e.g., 40 to 50 hours), most preferably about 45 hours (e.g., 45 hours)) to form an estolide containing a cyclic carbonate having the Formula

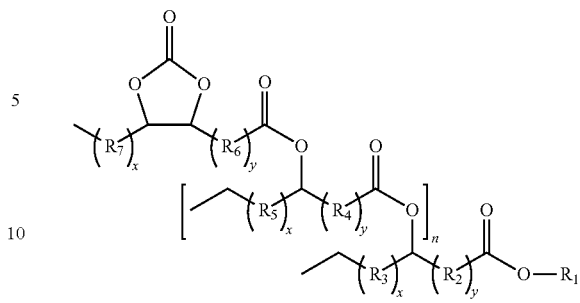

wherein x and y are each equal to 1 or greater than 1 (with an upper limit of 22) and x is independent from each occurrence (e.g., x could be 3 in one chain, but 4 or 5 in another chain; or x could be 1 in one chain, but 9 in another chain and 10 in yet another chain) and y is independent from each occurrence (e.g., y could be 3 in one chain, but 4 or 5 in another chain; or y could be 9 in one chain, and 1 in another chain and 3 in yet another), wherein n is 0-9, $R_1$ is H, or an linear alkyl chain (e.g., C1-C14; for example, methyl, ethyl, propyl, octyl; preferably methyl) or a branched alkyl chain (e.g., C1-C14; for example, 2-ethylhexyl, 1-methylpentyl, isopropyl; preferably 2-ethylhexyl) or

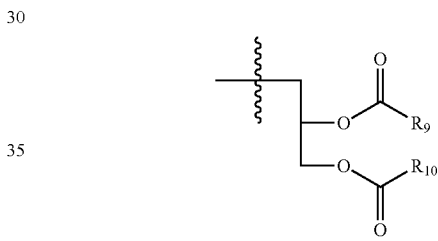

wherein $R_9$ and $R_{10}$ are independently selected from hydrogen and C-1 to C-36 hydrocarbon (preferably C12 to C22) which may be saturated or unsaturated, branched or straight chain, or substituted or unsubstituted (examples of ROO— include oleic, steric, butyric, lauric, myristic, palmitic, stearic, arachidic, behenic, lignoceric, oleic, linoleic, linolenic, petroselinic, ricinoliec, decanoic, octanoic, caproic acids; C-1 to C-36 hydrocarbon includes other fatty acid chain, or epoxidized fatty chain, or hydroxyl containing fatty chain, or carbonated fatty chain; carbonated fatty chain is defined as a hydrocarbon chain that contain a structure where two adjacent carbon atoms are bound to oxygen atoms that are bound to another carbon atom that is doubly bonded to an oxygen atoms; preferably $R_9$ and $R_{10}$ are substituted C18 hydrocarbon chains)), and $R_2$-$R_7$ are independently selected from —$CH_2$—, —C=C—, or

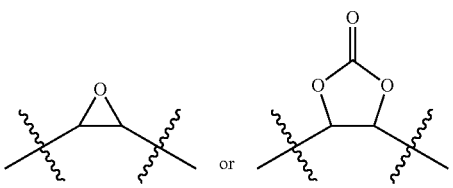 [SMILES: *C1OC1* ; *C1OC(=O)OC1*]

wherein residual epoxide or unsaturated groups may still be present or are not present.

The estolides containing a cyclic carbonate may be used to produce urethane containing estolides having the Formula 5

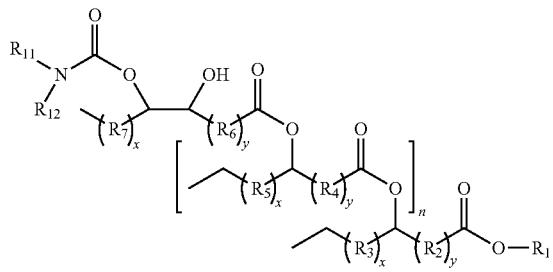

wherein x and y are each equal to 1 or greater than 1 (with an upper limit of 22) and x is independent from each occurrence (e.g., x could be 3 in one chain, but 4 or 5 in another chain; or x could be 1 in one chain, but 9 in another chain and 10 in yet another chain) and y is independent from each occurrence (e.g., y could be 3 in one chain, but 4 or 5 in another chain; or y could be 9 in one chain, and 1 in another chain and 3 in yet another), wherein n is 0-9, $R_1$ is H, or an linear alkyl chain (e.g., C1-C14; for example, methyl, ethyl, propyl, octyl; preferably methyl) or a branched alkyl chain (e.g., C1-C14; for example, 2-ethylhexyl, 1-methylpentyl, isopropyl; preferably 2-ethylhexyl) or

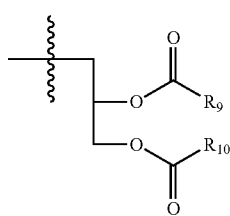

wherein $R_9$ and $R_{10}$ are independently selected from hydrogen and C1 to C36 hydrocarbon (preferably C12 to C22) which may be saturated or unsaturated, branched or straight chain, or substituted or unsubstituted (examples of ROO— include oleic, steric, butyric, lauric, myristic, palmitic, stearic, arachidic, behenic, lignoceric, oleic, linoleic, linolenic, petroselinic, ricinoliec, decanoic, octanoic, caproic acids; C-1 to C-36 hydrocarbon includes other fatty acid chain, or epoxidized fatty chain, or hydroxyl containing fatty chain, or carbonated fatty chain; carbonated fatty chain is defined as a hydrocarbon chain that contain a structure where two adjacent carbon atoms are bound to oxygen atoms that are bound to another carbon atom that is doubly bonded to an oxygen atoms; preferably $R_9$ and $R_{10}$ are substituted C18 hydrocarbon chains)), and $R_2$-$R_7$ are independently selected from —$CH_2$—, —C=C—, or

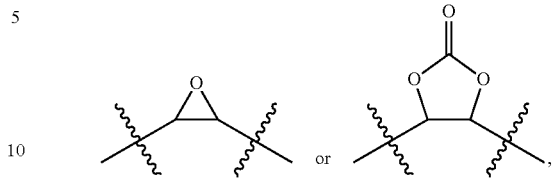

$R_{11}$ and $R_{12}$ are independently selected from H, any C1-C14 alkyl chain (preferably hexyl), any C1-C14 branched alkyl chain (preferably isopropyl, any C1-C14 (preferably hexyl) alkyl chain containing an amine or hydroxyl group (preferably 6-aminohexyl).

The urethane containing estolide may be made by reacting estolides containing a cyclic carbonate with an amine or diamine (e.g., examples of amine dihexylamine, 1,4-diaminobutane or 1,6-diaminohexane; about 0.1 to about 10 molar equivalents (e.g., 0.1 to 10 molar equivalents; preferably about 0.1 to about 5 molar equivalents (e.g., 0.1 to 5 molar equivalents), more preferably about 0.5 to about 2 equivalents (e.g., 0.5 to 2 molar equivalents) at temperatures of about 0° to about 150° C. (e.g., 0° to 150° C.; preferably about 10° to about 100° C. (e.g., 10° to 100° C.), more preferably about 15° to about 30° C. (e.g., 15° to 30° C.)) for about 0.1 to about 100 hours (e.g., 0.1 to 100 hours; preferably about 1 to about 40 hours (e.g., 1 to 40 hours), more preferably about 4 to about 12 hours (e.g., 4 to 12 hours)).

The amounts, percentages and ranges disclosed herein are not meant to be limiting, and increments between the recited amounts, percentages and ranges are specifically envisioned as part of the invention.

"Optional" or "optionally" means that the subsequently described event or circumstance may or may not occur, and that the description includes instances in which said event or circumstance occurs and instances where it does not. For example, the phrase "optionally comprising a defoaming agent" means that the composition may or may not contain a defoaming agent and that this description includes compositions that contain and do not contain a foaming agent.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

Unless defined otherwise, all technical and scientific terms used herein have the same meaning as commonly understood by one of ordinary skill in the art to which the invention belongs. As used herein, the term "about" refers to a quantity, level, value or amount that varies by as much as 30%, preferably by as much as 20%, and more preferably by as much as 10% to a reference quantity, level, value or amount. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

Examples

Materials, instruments, and equipment: Hydrogen peroxide as a 30% aqueous solution (Sigma-Aldrich, St. Louis, Mo.; A.C.S. Reagent), formic acid (Sigma-Aldrich, St. Louis, Mo.; 96%, A.C.S. reagent), toluene (Fisher, Fairlawn, N.J.; 99.9%), hexanes (Sigma-Aldrich, St. Louis, Mo.; >95%, HPLC grade), pentadecane (Sigma-Aldrich, St. Louis, Mo.; 99+%), sodium chloride (Fisher, Fairlawn, N.J.; A.C.S. Reagent), magnesium sulfate (J. T. Baker, Phillipsburg, N.J.; 99.8%), sodium sulfate (Fisher, Fairlawn, N.J.; certified A.C.S.), glacial acetic acid (Fisher, Fairlawn; NJ, 99.9%), chlorobenzene (Sigma-Aldrich, St. Louis, Mo.; 99%), crystal violet (Sigma-Aldrich, St. Louis, Mo.; 95%), hydrobromic acid (Fluka, St. Louis, Mo.; 33% in acetic acid), potassium hydrogen phthalate (Mallinckrodt, St. Louis, Mo.; 99.5%), tetrabutylammonium bromide (Sigma-Aldrich, St. Louis, Mo.; 99%), 1,4-diaminobutane (Alfa Aesar, Ward Hill, Mass.; 98+%), 1,6-diaminohexane (Alfa Aesar, Ward Hill, Mass.; 98+%) were used as received. Carbon dioxide (Ilmo, Jacksonville, Ill.; bone dry) was supplied in a pressurized tank with a dip tube. The reactor employed in the carbonation reactions was a 50 mL high pressure steel reactor (Parr, Moline, Ill.; 5500 mini and 4836 controller). Pressure was maintained by a high pressure syringe pump (Teledyne Isco, Lincoln, Nebr.; 260D).

The Fourier Transform infrared spectra (FTIR, Thermonicolet, Madison, Wis.; Nexus 470) reported herein were obtained by collecting 32 scans using a Smart Orbit accessory equipped with a diamond plate. The nuclear magnetic resonance (NMR) spectra were taken on a Bruker (Boston, Mass.) Avance 500 NMR spectrometer operating at 500 MHz for $^1$H and 125 MHz for $^{13}$C. The spectrometer was equipped with a 5 mm dual probe, and controlled by Bruker Icon NMR software.

Viscosity measurements were performed on a TA Instruments ARES controlled strain rheometer with 1 K FRTN1 transducer using TA Orchestrator software package 7.2.2.1. Initial runs were made at a constant temperature of 25° C. with varied shear rate, from 0.1 to 100 s$^{-1}$. Newtonian behavior (i.e. constant viscosity vs. further increases in sheer rate) was observed at shear rates >4 s$^{-1}$. Experiments run with a constant sheer rate of 100 s$^{-1}$ at varied temperatures were also performed. Oxirane values were determined following AOCS method Cd9-57. The substrate, 2-ethylhexyl estolide was used as a prototypical example for the synthesis of a chemically modified alkyl estolide.

Example 1

Epoxidation of 2-ethylhexyl estolide. Estolide epoxidation was performed as follows: In a 50 mL 3-necked flask, 20.1 g of 2-ethylhexyl estolide was combined with 11.2 g of formic acid. Hydrogen peroxide (16.4 g) was added drop wise while ensuring the temperature remained at 19° C. or below by using an ice bath. The reaction was stirred at 750 rpm overnight. The reaction solution was transferred to a 125 mL separatory funnel with 25 mL hexane, and the formic acid containing aqueous layer was removed. The product was washed 2× with saturated sodium bicarbonate solution, 2× with saturated sodium chloride solution, 3× with deionized water, and then dried over 3 g of magnesium sulfate which was removed by filtration. The solvent was removed with rotary evaporation and the liquid product (17.4 g) was isolated. The oxirane value of the product was determined by AOCS method Cd9-57 and gave a value of 1.52%. The $^1$H NMR of epoxidized 2-ethylhexyl estolide: δ 4.9-4.8 (m, 1.0H, —CH—OC=O—), 4.0 (d, 2.0H, —OCH$_2$—CH(CH$_2$)CH$_2$—), 2.9 (b, small impurity from epoxidized multiple unsaturates), 2.7-2.6 (t, 1.0H, CH$_2$—CH(O)CH—CH$_2$), 2.3-2.2 (m 4.1H, —CH$_2$(C=O)—O—CH— and —CH$_2$(C=O)—O—CH—) and 1.7-0.7 overlapping signals corresponding to hydrogens bound to carbons in the hydrocarbon chains. The $^{13}$C NMR: δ 174 (C=O), δ 173 (C=O), 74 (—CH—O—C=O), 67 (—O—CH$_2$—CH—), 59 (—CH$_2$—CH(O)CH—CH$_2$), 39 (—CH$_2$—CH(CH$_2$)—CH$_2$) and 35-10 overlapping signals corresponding to carbons in the hydrocarbon chains. The FTIR spectra (FIG. 3) shows the estolide peaks in addition to the expected epoxide signal at 895 cm$^{-1}$.

Carbonation of 2-ethylhexyl estolide. The carbonation of the epoxidized estolide was performed as follows: In a 25 mL high pressure reactor, 15.2 g of epoxidized estolide was combined with 0.77 g tetrabutylammonium bromide and brought to 100° C. and 10.03 MPa (1500 lb in$^{-2}$) of carbon dioxide pressure which is above its critical pressure of 7.38 MPa (1070 lb in$^{-2}$) at that temperature. The reaction was stirred at 300 rpm for 45 hours and then the reactor was cooled, depressurized slowly, and the product taken up in 20 mL of heptane. It was washed 2× with water and 2× with saturated sodium chloride solution, then dried over sodium sulfate, filtered, and the heptane was removed by rotary evaporation to give 9.65 g of product that was characterized. Both the he $^1$H NMR of carbonated 2-ethylhexyl estolide (FIG. 4, top), compared with that of the starting material, showed new signals proving the effectiveness of the carbonation reaction. The FTIR spectra (FIG. 3) showed the normal estolide peaks, the loss of the epoxide signal at 895 cm$^{-1}$, and a new strong carbonyl signal at 1807 cm$^{-1}$.

Example 2

Figure 6:
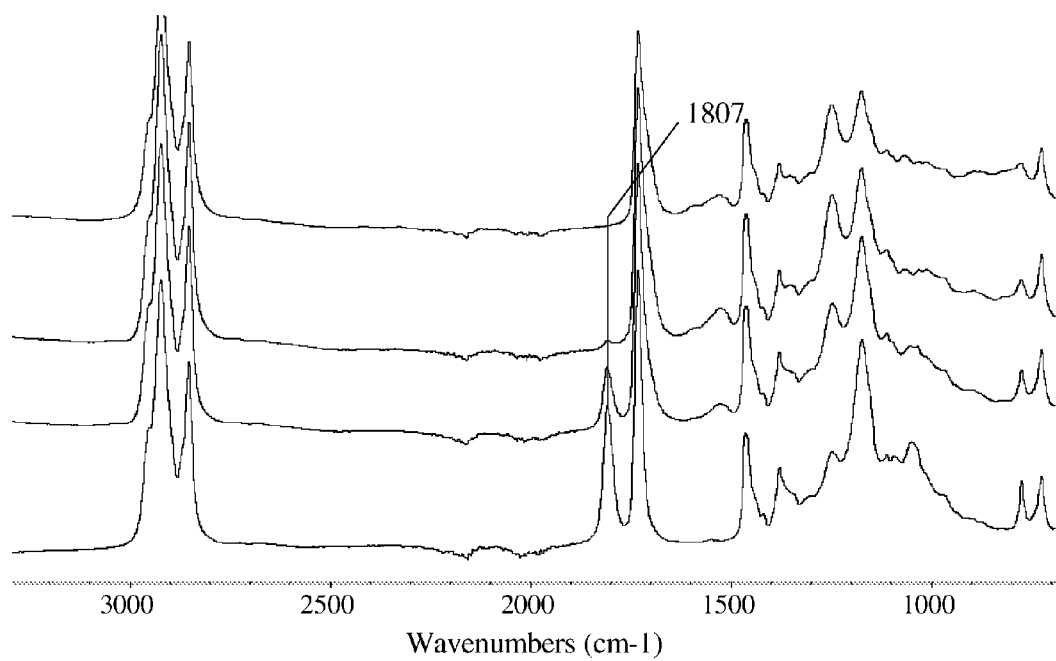
FIG. 6 shows the infrared spectra of carbonated 2-ethylhexyl estolide (bottom), with the addition of 1,6-diaminohexane, with excess carbonate (lower), near equimolar (middle), and excess amino groups (top) as described below.

Ring opening reaction of 2-ethylhexyl estolide with amines: The carbonated 2-ethylhexyl estolide was subjected to a ring opening reaction with 11,6-diaminohexane. For example, about 1 g of the estolide was stirred overnight at room temperature with 0.0590, 0.1462, or 0.2125 g of 1,6-diaminohexane. The product mixtures from the reaction were examined spectroscopically as shown in FIG. 6. A similar reaction was also performed with 1,4-diaminobutane with similar results.

Results and discussion. Synthesis of epoxidized estolide: The unsaturated sites of the starting oleic estolide were epoxidized using performic acid generated in situ from formic acid and hydrogen peroxide (FIG. 1). The epoxidation reaction progress was monitored by taking aliquots to determine the oxirane number. After overnight reaction the crude epoxidized estolide was isolated and the oxirane value was determined to be 1.52%, and demonstrated that the unsaturated sites of the estolide were surprisingly almost fully epoxidized based on the amount of unsaturation present in the starting estolide.

Figure 3:
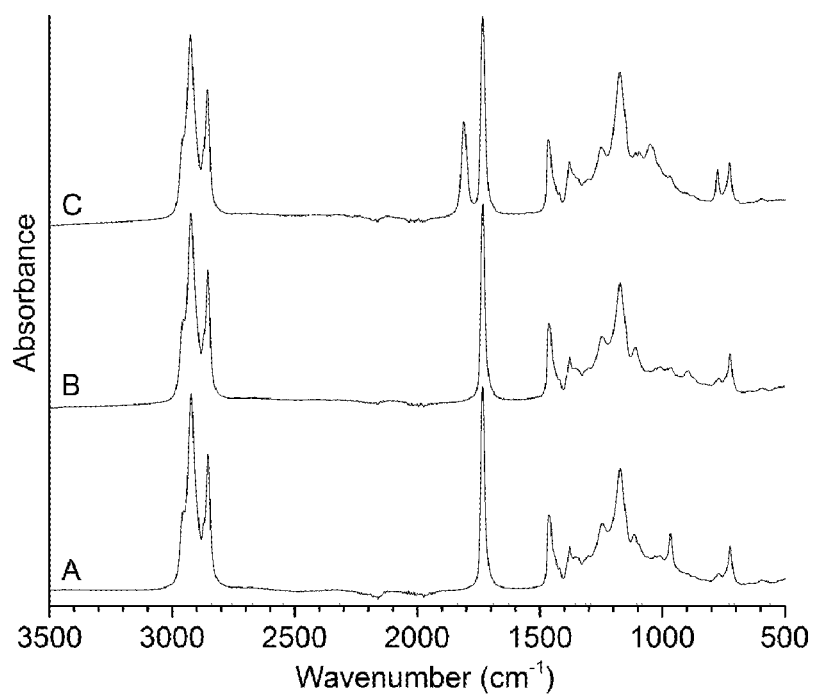
FIG. 3 shows the infrared spectra of 2-ethylhexyl estolide (bottom), epoxidized 2-ethylhexyl estolide (middle), and carbonated 2-ethylhexyl estolide (top) as described below.
Figure 4:
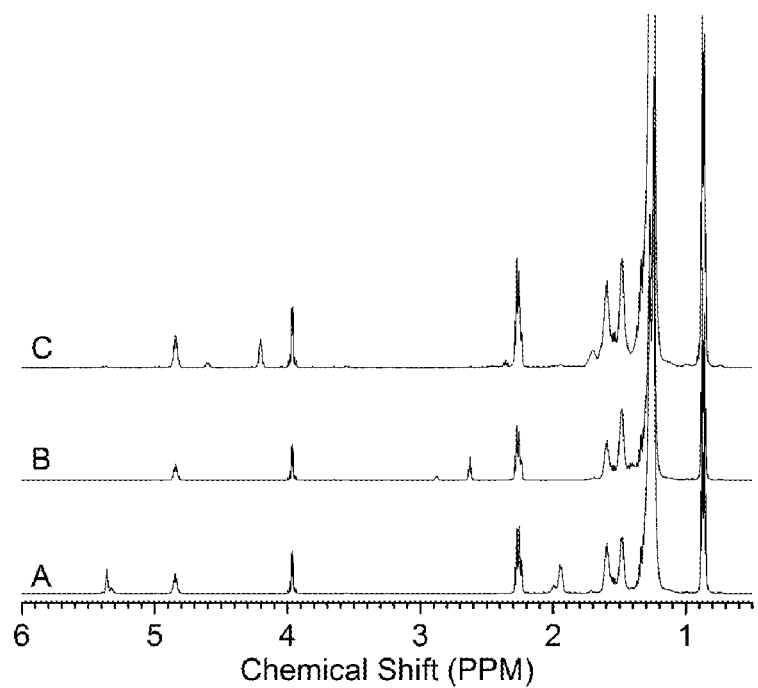
FIG. 4 shows the $^1$H NMR spectrum of 2-ethylhexyl estolide (bottom), epoxidized 2-ethylhexyl estolide (middle) and carbonated 2-ethylhexyl estolide (top) as described below.

Examination of the epoxidized estolide as compared to the starting oleic estolide by FT-IR spectroscopy is shown in FIG. 3. The epoxidized estolide was similar in the main characteristics with respect to the starting oleic estolide. The sharp C=O stretching of the estolide ester groups in both spectra were evident at 1733 cm$^{-1}$. In the starting oleic estolide, a slight shoulder can be observed above the 2923 cm$^{-1}$ peak which, without being bound by theory, is likely hydrogen stretching signals of the C=C which were masked by the preponderance of aliphatic CH stretching observed in the range of ~2800-3000 cm$^{-1}$. Additionally, in the oleic estolide spectrum a peak was observable at 966 cm$^{-1}$ that was, without being bound by theory, likely due to the CH out of plane bending of the C=C. In contrast, the epoxidized estolide spectrum showed the disappearance of these peaks and indicated that the double bonds had been surprisingly consumed during the reaction. The epoxidized estolide spectrum also surprisingly showed a new peak at 895 cm$^{-1}$ which was indicative of asymmetric stretching of the epoxide ring.

The $^1$H NMR spectrum of the oleic estolide (FIG. 4) showed the vinyl hydrogens at 5.3-5.5 ppm. The methine hydrogens of the ester groups along the alkyl chain backbone were evident at about 4.9 ppm while the methylene hydrogens of the 2-ethylhexyl adjacent to the ester oxygen atom were at 4.0 ppm. The α-methylene hydrogens next to the ester carbonyl groups were at about 2.2-2.3 ppm, the allylic hydrogens were at 1.9-2.0 ppm, aliphatic hydrogens of the alkyl chains and 2-ethylhexyl group between 1.0-1.7 ppm, and the terminal methyl groups of the alkyl chains and 2-ethylhexyl groups were at about 0.8-0.9 ppm. In the epoxidized estolide (spectra not shown), while the basic features of the estolide structure remained intact, new signals at ~2.6-2.7 ppm for the methine hydrogens of the epoxide ring appeared while the corresponding vinyl and allylic hydrogen signals were no longer visible, showing that the double bonds had been surprisingly converted into epoxide groups. The $^{13}$C NMR spectra (not shown) confirmed the conclusions drawn concerning the $^1$H NMR, namely that the carbon atoms of the double bonds in the oleic estolide at approximately 129 ppm had been reacted to derive the epoxy groups as evidenced by new signals at ~59 ppm.

Synthesis of carbonated estolide: Because the estolide structure contains a branched structure significantly different than a conventional vegetable oil, it was of interest to see if the ring could be opened with a catalyst. Surprisingly, treatment of the epoxidized estolide with supercritical carbon dioxide in the presence of tetrabutylammonium bromide gave the corresponding estolide containing 5-membered ring cyclic carbonate groups as a viscous liquid. The FTIR spectrum of the carbonated estolide (FIG. 3) showed an intense new peak at 1807 cm$^{-1}$ corresponding to the stretching vibrations of the carbonate's carbonyl group in addition to the carbonyl group stretching vibrations at 1732 cm$^{-1}$ of the ester groups. Additionally, the asymmetric stretching signal of the epoxide ring at 895 cm$^{-1}$ disappeared, confirming that the epoxide had been consumed during the reaction. This means that even with the estolide structures in the material, the epoxide group was surprisingly the site of reaction.

The main features of interest in the $^1$H NMR spectrum of the carbonated estolide (FIG. 4) were absence of the epoxide's methine hydrogens between ~2.6-2.7 ppm, indicating that the epoxide group had been reacted and the subsequent formation of two new peaks at 4.3-4.4 ppm and 4.60 ppm with the former signal being of greater intensity than the latter. These signals were attributable to the methine hydrogens of the five-membered cyclic carbonate rings. The $^{13}$C NMR (not shown) also confirmed the formation of the carbonate group on the estolide chain by the loss of the epoxide carbon signals at 59 ppm and the formation of two new signals at 82 ppm and 155 ppm, corresponding to the methine carbon atoms of the carbonate ring and the carbonate carbonyl group, respectively.

Figure 5:
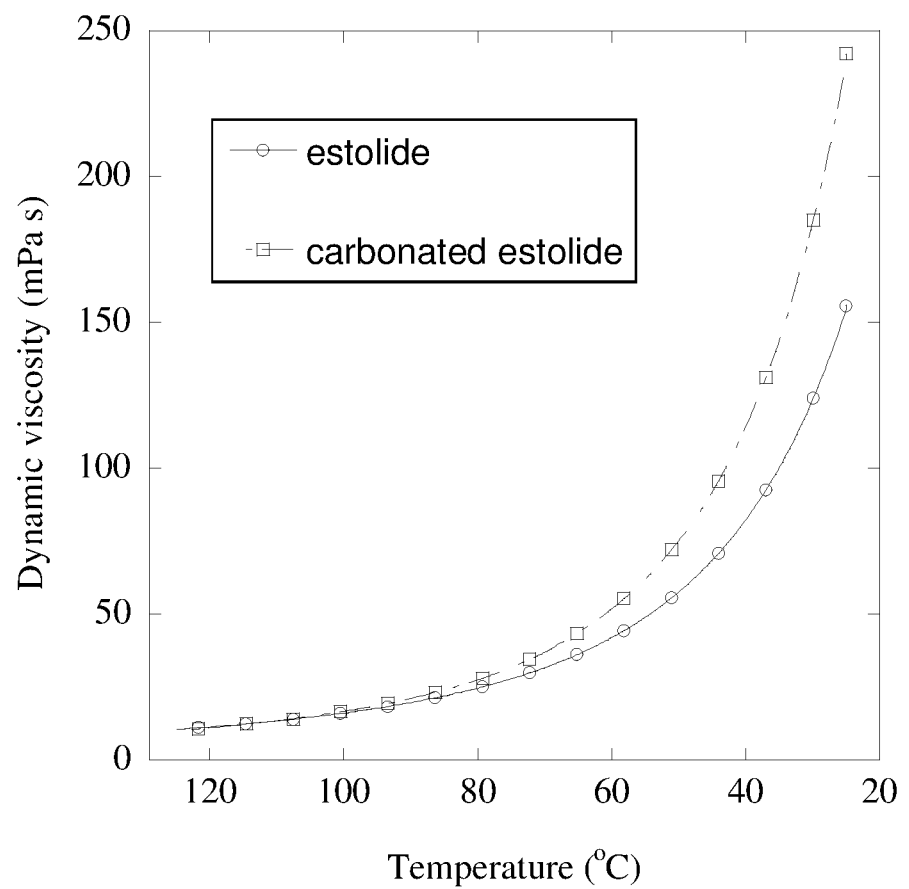
FIG. 5 shows a plot of dynamic viscosity vs temperature for 2-ethylhexyl estolide (○), and carbonated 2-ethyhexyl estolide (□) as described below.

Viscosity of carbonated estolide: Viscosity data (FIG. 5) surprisingly demonstrated the thickening of the carbonated estolide compared to the starting material. These materials were heated in a rheometer and the viscosity was observed as the samples were allowed to cool. At 125° C., the viscosities of the estolide and the carbonated estolide were each just over 10 mPa s, but the difference was quite apparent at 25° C. where the carbonate was surprisingly more than 1.5 times as viscous, 242 vs 155 mPa s. Surprisingly, the 2-ethylhexyl estolide had an identical viscosity before and after heating in the rheometer, whereas the carbonate was 22% higher after heating, possibly due, without being bound by theory, to a minor amount of residual solvent in the carbonated material.

Figure 2:
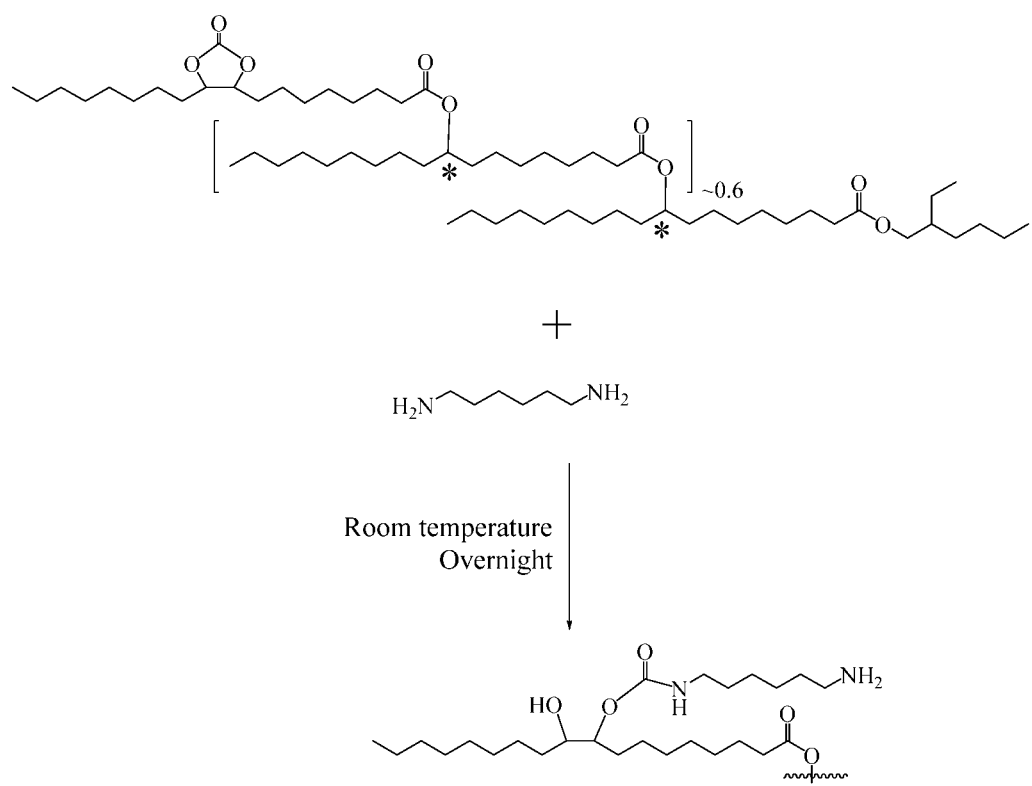
FIG. 2 shows ring opening of a carbonated estolide using an amine as described below.

Ring opening of carbonated estolide with an amine: We surprisingly found that cyclic carbonates can be used for isocyanate free polyurethanes. The key to this application is the ability of the carbonate to react with a terminal amine group (FIG. 2) to form a urethane moiety and hydroxyl group on the estolide chain. This reaction was demonstrated by the addition of 1,6-diaminohexane at three different levels. The FT-IR spectra (FIG. 6) showed the decrease in the carbonyl signal at 1807 cm$^{-1}$. At low levels of the added amine, where there was an excess of carbonate, the peak was decreased significantly. A very small signal was still observed when amine and carbonate were in close molar amounts, and which was completely gone when excess amine was used. A similar phenomenon was noted in the $^{13}$C NMR where the size of the δ 82 ppm signal was diminished proportionally as the amine reacted with the carbonate group.

Figure 7:
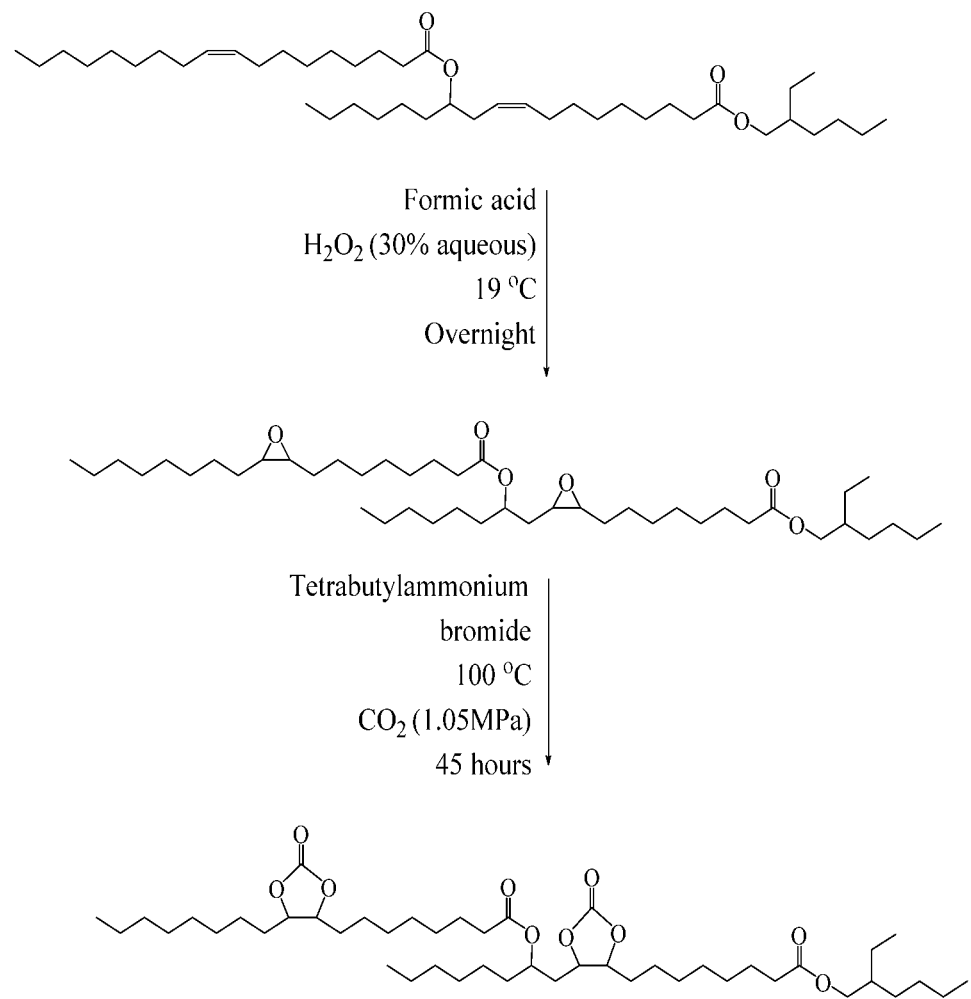
FIG. 7 shows the carbonation route of the estolide of oleic acid and 2-ethylhexyl ricinoleate using an epoxide intermediate as described below.
Figure 8:
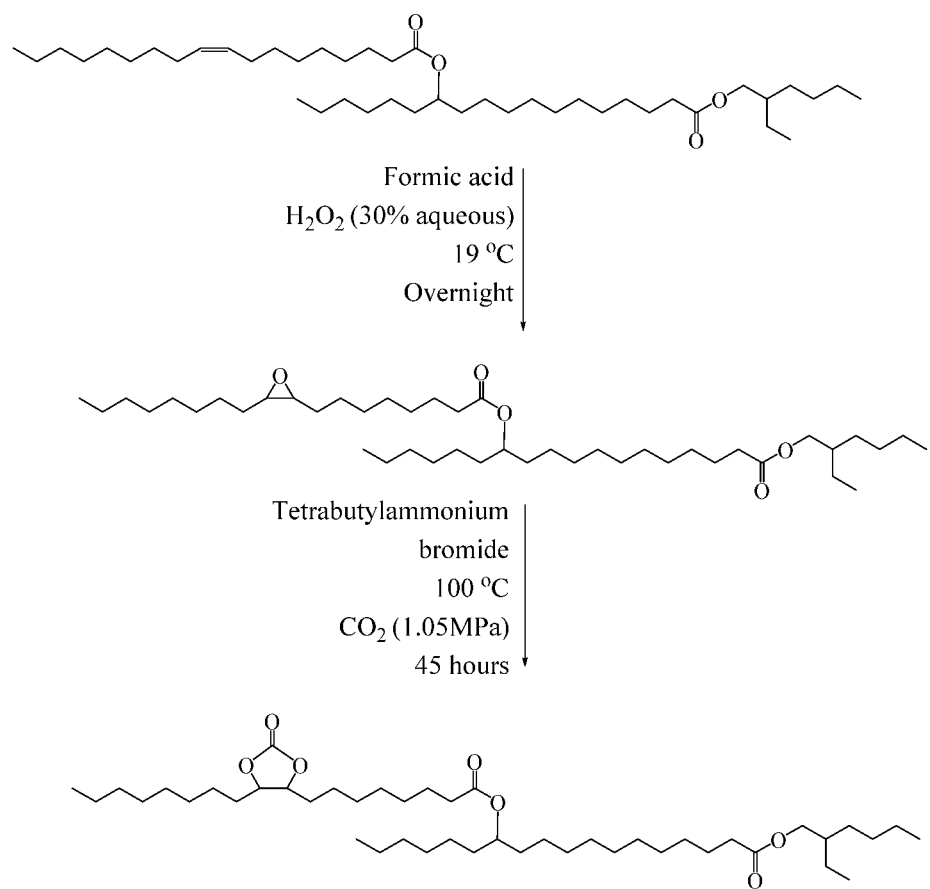
FIG. 8 shows the carbonation route of the estolide of oleic acid and 2-ethylhexyl ester of 12-hydroxy stearate using an epoxide intermediate as described below.
Figure 9:
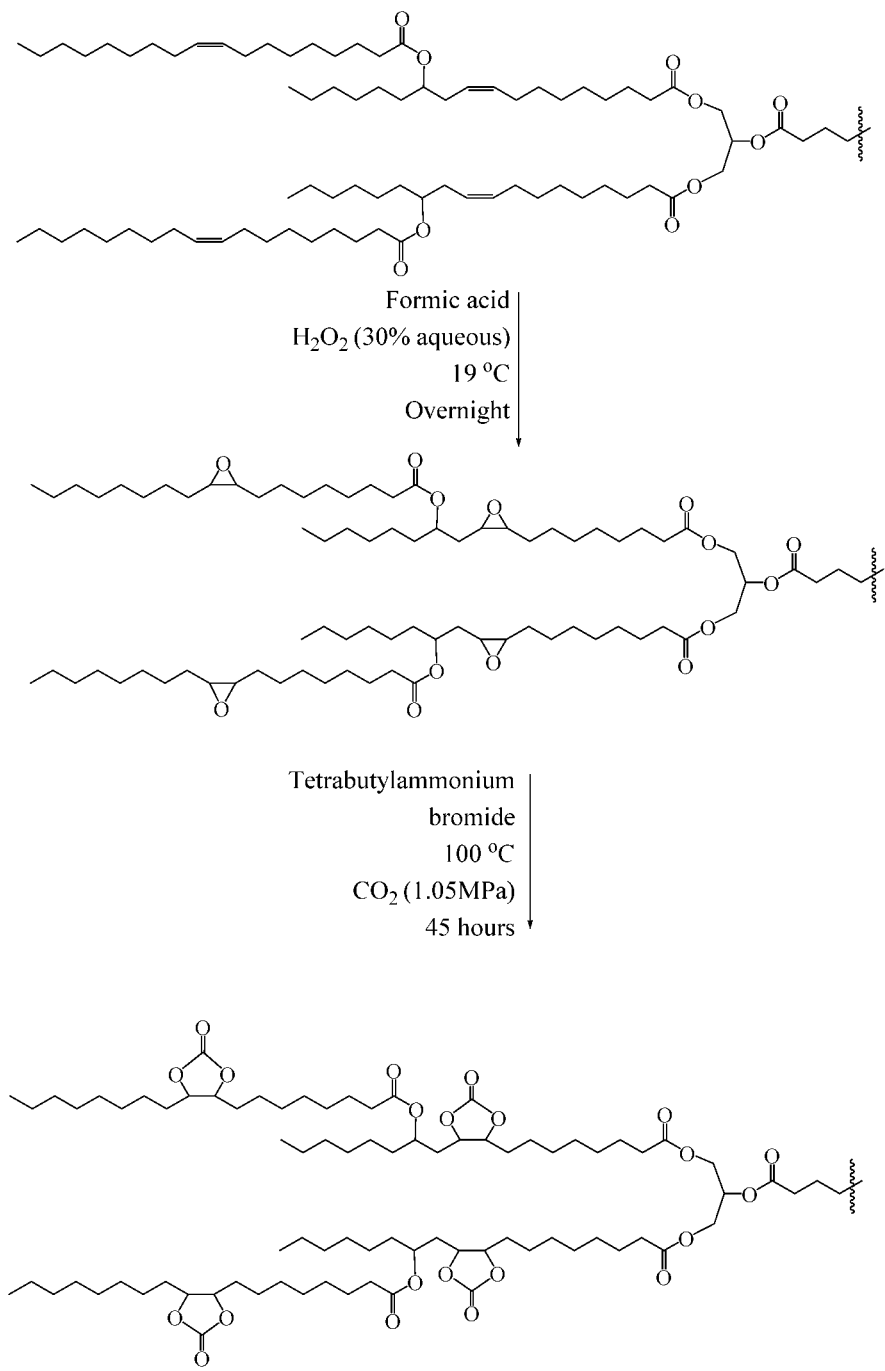
FIG. 9 shows the carbonation route of the estolide of oleic acid and castor oil using an epoxide intermediate as described below.

In analogous examples, carbonated materials from estolides of other sources were also made, including those based on the oleic acid and 2-ethylhexyl esters of ricinoleic acid (FIG. 7), oleic acid and the 2-ethylhexyl esters of 12-hydroxy stearic acid (FIG. 8), and oleic acid and castor oil with the triacylglycrol still intact (FIG. 9).

Thus the chemical modification of unsaturated estolides to epoxides and carbonate containing materials could surprisingly be performed with simple reagents. This is a viable strategy for increasing the viscosity of the material which may be used as lubricants, hydraulic fluids, or gear oils. It also gives estolides containing a new functional moiety that can be further modified. For example, ring opening of the carbonate moiety with an amine gave an urethane linkage that may be used to prepare polyurethane coatings without the use of toxic isocyanates and demonstrates the overall utility of carbonated estolides.

All of the references cited herein, including U.S. Patents, are incorporated by reference in their entirety. Also incorporated by reference in their entirety are the following references: Adhvaryu, A., et al., Ind. Eng. Chem. Res., 45: 3735-3740 (2006); (Clements, J. H., Ind. Eng. Chem. Res., 42: 663-674 (2003); Wilkes et al., 2006); Findley, T. W., et al., J. Am. Chem. Soc., 67: 412-414 (1945); Findley et al., 1945; Bueno-Ferrer, C., et al., Polymer Degradatoin and Stability, 95: 2207-2212 (2010); La Scala, J., and R. P. Wool, J. Am. Oil Chem. Soc., 79: 373-378 (2002); Moser, B. R., and S. Z. Erhan, J. Am. Oil Chem. Soc., 83: 959-963 (2006); Schmitz, W. R., and J. G. Wallace, J. Am. Oil Chem. Soc., 31: 363-365 (1954); U.S. Pat. No. 6,316,649; U.S. Pat. No. 7,045,577 (2006); U.S. Pat. No. 8,258,326.

The term "consisting essentially of" excludes additional method (or process) steps or composition components that substantially interfere with the intended activity of the method (or process) or composition.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Pour points of the example materials and the oxirane values where applicable.

|  | Example 1 | Example 3 | Example 4 | Example 5 |
|---|---|---|---|---|
| Olefinic | | | | |
| Pour point (° C.) | −39 | −54 | −54 | −39 |
| Epoxidized | | | | |
| Pour point (° C.) | −33 | −48 | −51 | −24 |
| Oxirane value (%) | 1.5 | 2.7 | 2.3 | 3.9 |
| Carbonated | | | | |
| Pour point (° C.) | −33 | −18 | −24 | 9 |

TABLE 2

Dynamic viscosities of the example materials.

| Dynamic viscosity (mPa s) | 25° C. | 40° C. | 100° C. |
|---|---|---|---|
| Example 1 | | | |
| Olefinic | 164 | 82 | 11 |
| Epoxidized | 207 | 95 | 10 |
| Carbonated | 358 | 155 | 15 |
| Example 3 | | | |
| Olefinic | 76 | 39 | 6 |
| Epoxidized | 152 | 70 | 7 |
| Carbonated | 753 | 282 | 17 |
| Example 4 | | | |
| Olefinic | 78 | 41 | 7 |
| Epoxidized | 124 | 60 | 7 |
| Carbonated | 409 | 168 | 13 |
| Example 5 | | | |
| Olefinic | 262 | 125 | 15 |
| Epoxidized | 1155 | 458 | 35 |
| Carbonated | 22431 | 5937 | 173 |

We claim:

1. An estolide containing a cyclic carbonate having the Formula

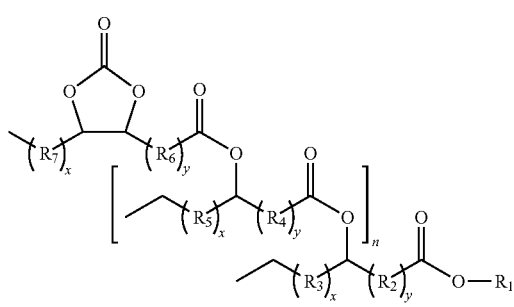

wherein x and y are each equal to 1 or greater than 1 and x is independent from each occurrence and y is independent from each occurrence, wherein n is 0-9, $R_1$ is H, or an linear alkyl chain or a branched alkyl chain or

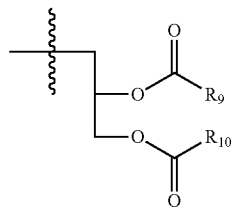

wherein $R_9$ and $R_{10}$ are independently selected from hydrogen and C-1 to C-36 hydrocarbon which may be saturated or unsaturated, branched or straight chain, or substituted or unsubstituted, and $R_2$-$R_7$ are independently selected from —$CH_2$—, —C═C—, or

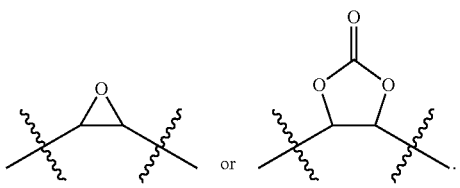 [SMILES: *C1OC1* ; *C1OC(=O)OC1*]

2. A method of making an estolide containing a cyclic carbonate, said method comprising
   (a) forming epoxidized estolide by reacting formic acid and $H_2O_2$ with at least one estolide compound of the Formula

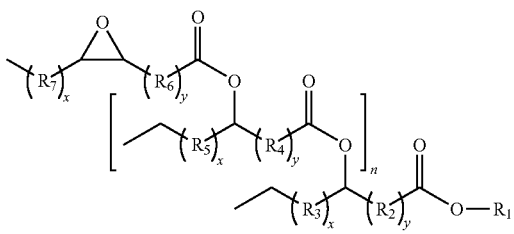

wherein x and y are each equal to 1 or greater than 1 and x is independent from each occurrence and y is independent from each occurrence, wherein n is 0-9, $R_1$ is H, or an linear alkyl chain or a branched alkyl chain or

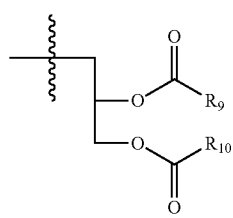

wherein $R_9$ and $R_{10}$ are independently selected from hydrogen and C-1 to C-36 hydrocarbon which may be saturated or unsaturated, branched or straight chain, or substituted or unsubstituted, and $R_2$-$R_7$ are independently selected from —$CH_2$—, —C=C—, or

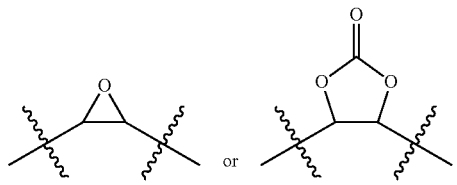 [SMILES: *C1OC1* ; *C1OC(=O)OC1*]

(b) reacting said epoxidized estolide with an alkylammonium salt and pressurized $CO_2$ to form an estolide containing a cyclic carbonate having the Formula

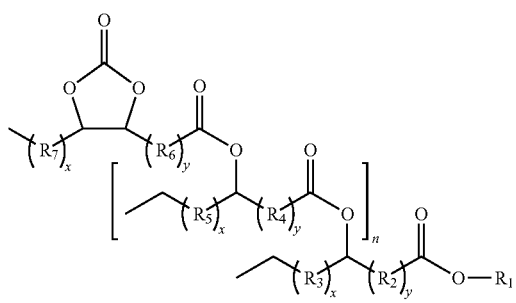

wherein x and y are each equal to 1 or greater than 1 and x is independently from each occurrence and y is independently from each occurrence, wherein n is 0-9, $R_1$ is H, or an linear alkyl chain or a branched alkyl chain or

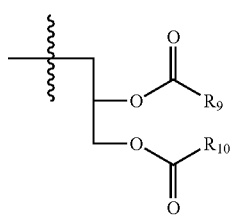

wherein $R_9$ and $R_{10}$ are independently selected from hydrogen and C-1 to C-36 hydrocarbon which may be saturated or unsaturated, branched or straight chain, or substituted or unsubstituted, and $R_2$-$R_7$ are independently selected from —$CH_2$—, —C=C—, or

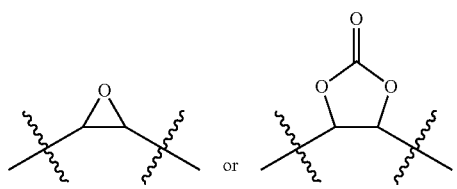 [SMILES: *C1OC1* ; *C1OC(=O)OC1*]

wherein residual epoxide or unsaturated groups may still be present.

3. The method according to claim 2, wherein residual epoxide or unsaturated groups are not present.

4. An estolide containing a cyclic carbonate having the Formula

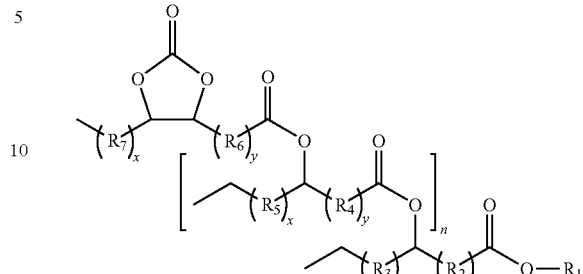

wherein x and y are each equal to 1 or greater than 1 and x is independently from each occurrence and y is independently from each occurrence, wherein n is 0-9, $R_1$ is H, or an linear alkyl chain or a branched alkyl chain or

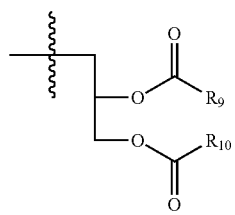

wherein $R_9$ and $R_{10}$ are independently selected from hydrogen and C-1 to C-36 hydrocarbon which may be saturated or unsaturated, branched or straight chain, or substituted or unsubstituted, and $R_2$-$R_7$ are independently selected from —$CH_2$—, —C=C—, or

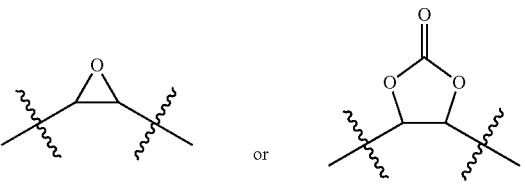 [SMILES: *C1OC1* ; *C1OC(=O)OC1*]

said estolide containing a cyclic carbonate prepared by the method according to claim 2.

5. A urethane containing estolide having the Formula

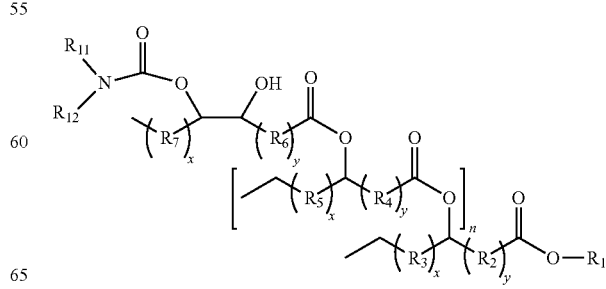

wherein x and y are each equal to 1 or greater than 1 and x is independent from each occurrence and y is independent from each occurrence, wherein n is 0-9, $R_1$ is H, or an linear alkyl chain or a branched alkyl chain or

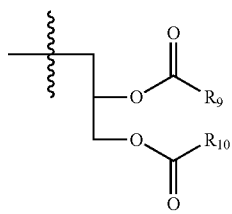

wherein $R_9$ and $R_{10}$ are independently selected from hydrogen and C-1 to C-36 hydrocarbon which may be saturated or unsaturated, branched or straight chain, or substituted or unsubstituted, and $R_2$-$R_7$ are independently selected from —$CH_2$—, —C═C—, or

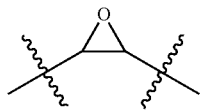 or 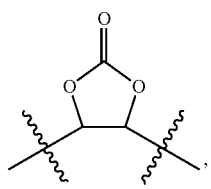, $R_{11}$ and $R_{12}$ are independently selected from H, any alkyl chain [C1-C14], any branched alkyl chain [C1-C14], any alkyl chain containing an amine or hydroxyl group [C1-C14].

6. A method to making a urethane containing estolide, said method comprising (a) forming epoxidized estolide by reacting formic acid and $H_2O_2$ with at least one estolide compound of the Formula

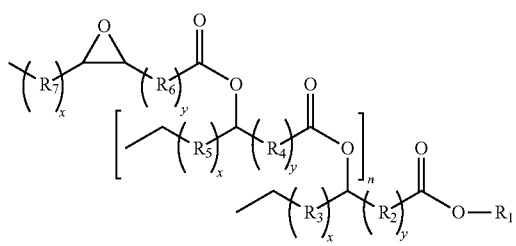

wherein x and y are each equal to 1 or greater than 1 and x is independently from each occurrence and y is independently from each occurrence, wherein n is 0-9, $R_1$ is H, or an linear alkyl chain or a branched alkyl chain or

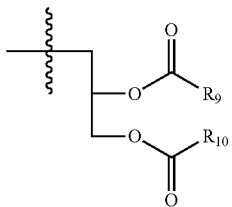

wherein $R_9$ and $R_{10}$ are independently selected from hydrogen and C-1 to C-36 hydrocarbon which may be saturated or unsaturated, branched or straight chain, or substituted or unsubstituted, and $R_2$-$R_7$ are independently selected from —$CH_2$—, —C═C—, or

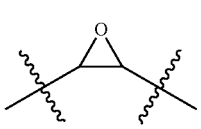 or 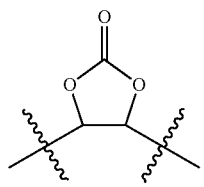

(b) reacting said epoxidized estolide with an alkylammonium salt and pressurized $CO_2$ to form an estolide containing a cyclic carbonate having the Formula

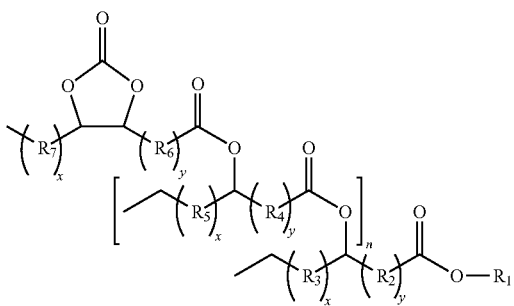

wherein x and y are each equal to 1 or greater than 1 and x is independently from each occurrence and y is independently from each occurrence, wherein n is 0-9, $R_1$ is H, or an linear alkyl chain or a branched alkyl chain or

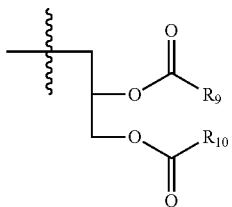

wherein $R_9$ and $R_{10}$ are independently selected from hydrogen and C-1 to C-36 hydrocarbon which may be saturated or unsaturated, branched or straight chain, or substituted or unsubstituted, and $R_2$-$R_7$ are independently selected from —$CH_2$—, —C=C—, or

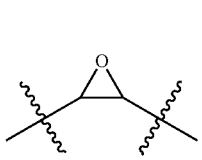 or 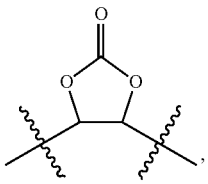, (c) and reacting said estolide containing a cyclic carbonate with an amine or diamine to form a urethane containing estolide having the Formula

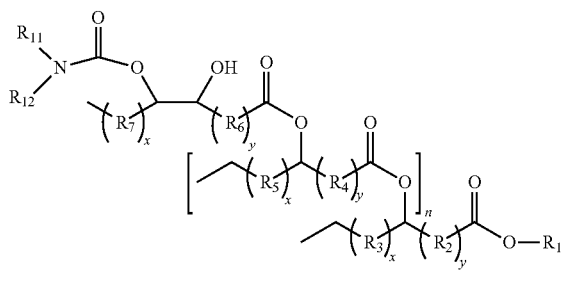

$R_{11}$ and $R_{12}$ are independently selected from H, any alkyl chain [C1-C14], any branched alkyl chain [C1-C14], any alkyl chain containing an amine or hydroxyl group [C1-C14].

7. A urethane containing estolide having the Formula

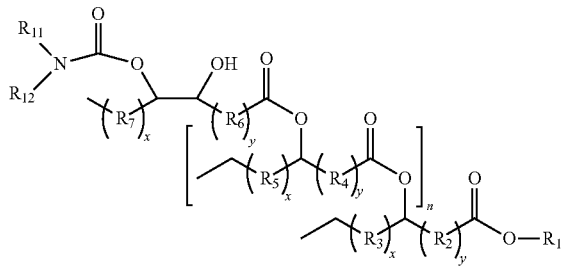

wherein x and y are each equal to 1 or greater than 1 and x is independently from each occurrence and y is independently from each occurrence, wherein n is 0-9, $R_1$ is H, or an linear alkyl chain or a branched alkyl chain or

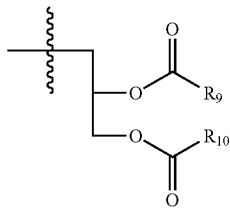

wherein $R_9$ and $R_{10}$ are independently selected from hydrogen and C-1 to C-36 hydrocarbon which may be saturated or unsaturated, branched or straight chain, or substituted or unsubstituted, and $R_2$-$R_7$ are independently selected from —$CH_2$—, —C=C—, or

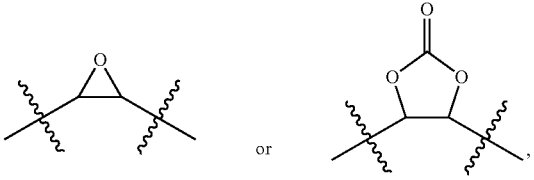 [SMILES: *C1OC1* ; *C1OC(=O)OC1*], $R_{11}$ and $R_{12}$ are independently selected from H, any alkyl chain [C1-C14], any branched alkyl chain [C1-C14], any alkyl chain containing an amine or hydroxyl group [C1-C14], produced the method of claim 6.

* * * * *